United States Patent
Yarger

Patent Number: 5,545,169
Date of Patent: Aug. 13, 1996

[54] LAPAROSCOPIC DELIVERY DEVICE

[76] Inventor: Richard J. Yarger, 4908 Douglas Dr., Yakima, Wash. 98908

[21] Appl. No.: 292,567

[22] Filed: Aug. 19, 1994

Related U.S. Application Data

[63] Continuation of Ser. No. 41,504, Apr. 1, 1993, abandoned.

[51] Int. Cl.$^6$ .............................................. A61F 11/00
[52] U.S. Cl. .................................................... 606/108
[58] Field of Search ............................ 606/1, 146, 167, 606/170, 180, 108, 184, 185; 604/19, 22, 26, 30, 164, 171, 169, 264, 263, 272, 284, 905; 128/749–754, 20

[56] References Cited

U.S. PATENT DOCUMENTS

| | | | |
|---|---|---|---|
| Re. 31,272 | 6/1983 | Pevsner | 604/28 |
| 636,637 | 11/1899 | Cooke | 604/13 |
| 700,139 | 5/1902 | Fuller | 604/13 |
| 1,120,549 | 12/1914 | Schellberg | 604/171 |
| 1,456,828 | 5/1923 | Pistor | 604/13 |
| 2,524,195 | 10/1950 | Hoover | |
| 2,711,734 | 6/1955 | Moe | |
| 3,034,508 | 5/1962 | Nalle, Jr. | |
| 3,154,080 | 10/1964 | Rowan et al. | |
| 3,561,445 | 2/1971 | Katerndahl | |
| 3,589,368 | 6/1971 | Jackson et al. | |
| 3,630,198 | 12/1971 | Henkin | |
| 3,703,174 | 11/1972 | Smith | |
| 3,826,256 | 7/1974 | Smith | |
| 3,982,544 | 9/1976 | Dyck | |
| 4,342,313 | 8/1982 | Chittenden | |
| 4,652,256 | 3/1987 | Vaillancourt | 604/52 |
| 4,655,750 | 4/1987 | Vaillancourt | 604/165 |
| 4,767,409 | 8/1988 | Brooks | 604/171 |
| 4,834,723 | 5/1989 | Sheridan et al. | 604/274 |
| 4,906,232 | 3/1990 | Reynolds | 604/171 |
| 4,944,728 | 7/1990 | Carrell et al. | 604/164 |
| 5,074,840 | 12/1991 | Yoon | 604/15 |
| 5,112,321 | 5/1992 | Hiltebrandt | 604/264 |
| 5,143,082 | 9/1992 | Kindberg et al. | 606/151 |
| 5,149,326 | 9/1992 | Woodgrift et al. | 604/163 |
| 5,190,555 | 3/1993 | Wetter et al. | 606/127 |
| 5,224,930 | 7/1993 | Spaeth et al. | 606/167 |
| 5,234,411 | 8/1993 | Vaillancourt | 604/171 |
| 5,263,969 | 11/1993 | Phillips | 606/108 |
| 5,312,416 | 5/1994 | Spaeth et al. | 606/113 |

FOREIGN PATENT DOCUMENTS 3511-448-A1  10/1986  Germany.

Primary Examiner—Gary Jackson
Assistant Examiner—Glenn Dawson
Attorney, Agent, or Firm—Christensen, O'Connor, Johnson and Kindness PLLC

[57] ABSTRACT

A delivery device (10) is used to deliver solid objects into the intra-abdominal cavity (12) of a patient through a previously inserted access port (16) while substantially preventing the escape of gases therefrom while using the device (10). The device includes a magazine (40) to substantially contain the object (42) prior to introduction into the intra-abdominal cavity (12). The magazine (40) is connected to a fitting (36) that connects the magazine to the access port (16). The object (42) is then introduced into the intra-abdominal cavity (12) through the fitting (36).

6 Claims, 5 Drawing Sheets

5,545,169

LAPAROSCOPIC DELIVERY DEVICE

This application is a continuation application based on prior application Ser. No. 08/041,504, filed on Apr. 1, 1993, now abandoned.

FIELD OF THE INVENTION

The present invention relates to devices which are used to introduce objects into the body of a patient during a laparoscopic medical procedure, through an access port that has previously been inserted into the patient.

BACKGROUND OF THE INVENTION

Laparoscopic medical procedures are accomplished through access ports. That is, small incisions are made in the patient, and an access port is inserted in each incision, giving medical personnel access to the interior of the body. Medical personnel then insert cameras and instruments through the access ports to perform the medical procedure.

When a laparoscopic procedure occurs within the intra-abdominal cavity of a patient, it is common to pressurize the cavity with a gas to enable the camera to provide medical personnel with a better view of the body's interior and to provide more room to perform the medical procedure. Usually, the access ports are constructed with valves which may be closed when the patient's intra-abdominal cavity is pressurized so that the gas cannot escape, and thus, deflate this space. In addition, the access ports normally have internal seals that seal against laparoscopic surgical instruments extending through the ports. Hence, pressurization gas is substantially prevented from escaping from the intra-abdominal cavity during the insertion and use of laparoscopic surgical instruments through the access ports.

A known problem, however, occurs when objects must be introduced through the access port into the body's interior that are significantly smaller in cross section than the internal diameters of the access ports so that the seals do not seal against the objects after the intra-abdominal cavity has been pressurized. The problem is that the pressurization gas escapes while the object is being introduced through the access port. The present invention addresses this problem by making it possible to insert such objects through the access port while substantially preventing the escape of the pressurization gas.

Typically, surgical procedures require the insertion of a drainage tube to drain the surgical site while the patient is recovering from surgery. In use, the distal end of the drainage tube is located at the surgical site in the patient's body and the proximal end is connected to an exterior suction/collection device. The drainage tube is placed in position by threading the proximal end of the drainage tube through a first access port and then partially out a second access port site until the distal end of the tube is inserted into the intra-abdominal cavity whereupon the distal end of the tube is positioned at the surgical site. Alternatively, the entire drainage tube is threaded into the intra-abdominal cavity and the distal end of the tube positioned at the desired location before the proximal end of the tube is withdrawn through a second access port site. The skin of the patient is sutured to the drainage tube in order to retain the tube and assist in preventing fluid leakage.

A problem with the above-described procedure is that the pressurization gas escapes through the gap between the internal diameter of the access port and the exterior of the drainage tube, due to the relatively small diameter of the drainage tube. As the drainage tube is hollow, the pressurization gas also escapes through the tube itself.

The foregoing only is one specific example of the problems that the present invention addresses. The present invention may be used to insert into the body different kinds of objects required in the course of laparoscopic surgery, other than drainage tubes, while substantially preventing the escape of the pressurization gas. Such other kinds of objects, by way of non-exclusive example, include plastic specimen bags, fabric material for surgical repairs of a hernia, sponges, etc.

SUMMARY OF THE INVENTION

The present invention provides a delivery device for introducing solid objects into the intra-abdominal cavity of a patient during a laparoscopic medical procedure. The objects are introduced through an access port previously inserted into the intra-abdominal cavity to provide access therein. Introduction of the object is accomplished while substantially preventing the escape of gases from the intra-abdominal cavity while the invention is being used.

Accordingly, a magazine is provided to substantially contain the object prior to introduction of the object into the intra-abdominal cavity. The magazine forms an enclosure, open at one end, with walls that are substantially impervious to the passage of gases. A fitting is also provided that connects the open end of the magazine to the access port so that there is communication between the magazine and the intra-abdominal cavity, but such that the escape of gases from the intra-abdominal cavity through the device is substantially prevented. A seal is formed between the fitting and the access port that substantially prevents the escape of gases from the intra-abdominal cavity through the access port to the environment Moreover, while the object previously loaded into the magazine is being introduced into the intra-abdominal cavity, the integrity of the seal between the fitting and the access port is maintained to substantially prevent the escape of gases therebetween.

In an alternative embodiment, the magazine is composed of a flexible, collapsible material. This embodiment may include a rod-like instrument partially inserted through the magazine along the longitudinal axis of the instrument, so that the first end of the instrument is inside the magazine, while the second end is outside of the magazine. The instrument may then be used to introduce an object through the fitting and the access port into the intra-abdominal cavity of the patient.

In another alternative embodiment, the magazine may be comprised of a first section and a second section that telescopically engage one another. Thus, the volume of the magazine is expandable to substantially contain the object by partially telescopically withdrawing the first section of the magazine from the second section. In this embodiment, it is also possible to substantially expel the object from the magazine by reducing the volume in the magazine. This expulsion is accomplished by partially telescopically inserting the first section further into the second section.

Further, in addition to the above-described embodiments of delivery devices, the present invention includes a method for introducing solid objects into the intra-abdominal cavity of a patient through a previously inserted access port while substantially preventing the escape of gases therefrom. The method comprises the steps of first placing an object in a magazine to contain the object that is open at one end and is substantially impervious to the passage of gases. Second, the open end of the magazine is sealed to the access port to enable the object to be expelled from the magazine, but still forming a seal with the access port to substantially prevent the escape of gases from the intra-abdominal cavity through the access port to the environment. In addition, gases are substantially prevented from escaping from the intra-abdominal cavity through the delivery device itself. Third, the desired object is introduced into the intra-abdominal cavity while substantially maintaining the seal between the magazine and the access port, and while substantially preventing the escape of gases through the magazine from the intra-abdominal cavity.

In this method, the step of introducing the object into the intra-abdominal cavity may be accomplished by attaching the magazine to a fitting so that a leading portion of the object being delivered extends from the magazine through the fitting. Furthermore, the object is arranged so that a leading portion of the object extends beyond the forward end of the fitting (the end opposite from the magazine). The object is then introduced into the intra-abdominal cavity by grasping the leading end of the object with an instrument previously inserted into the intra-abdominal cavity through a second access port. The object is then drawn into the intra-abdominal cavity by manipulation of the instrument.

BRIEF DESCRIPTION OF THE DRAWINGS

The foregoing aspects and many of the attendant advantages of this invention will become more readily appreciated as the same becomes better understood by reference to the following detailed description, when taken in conjunction with the accompanying drawings, wherein.

DETAILED DESCRIPTION OF THE PREFERRED EMBODIMENT

Figure 1:
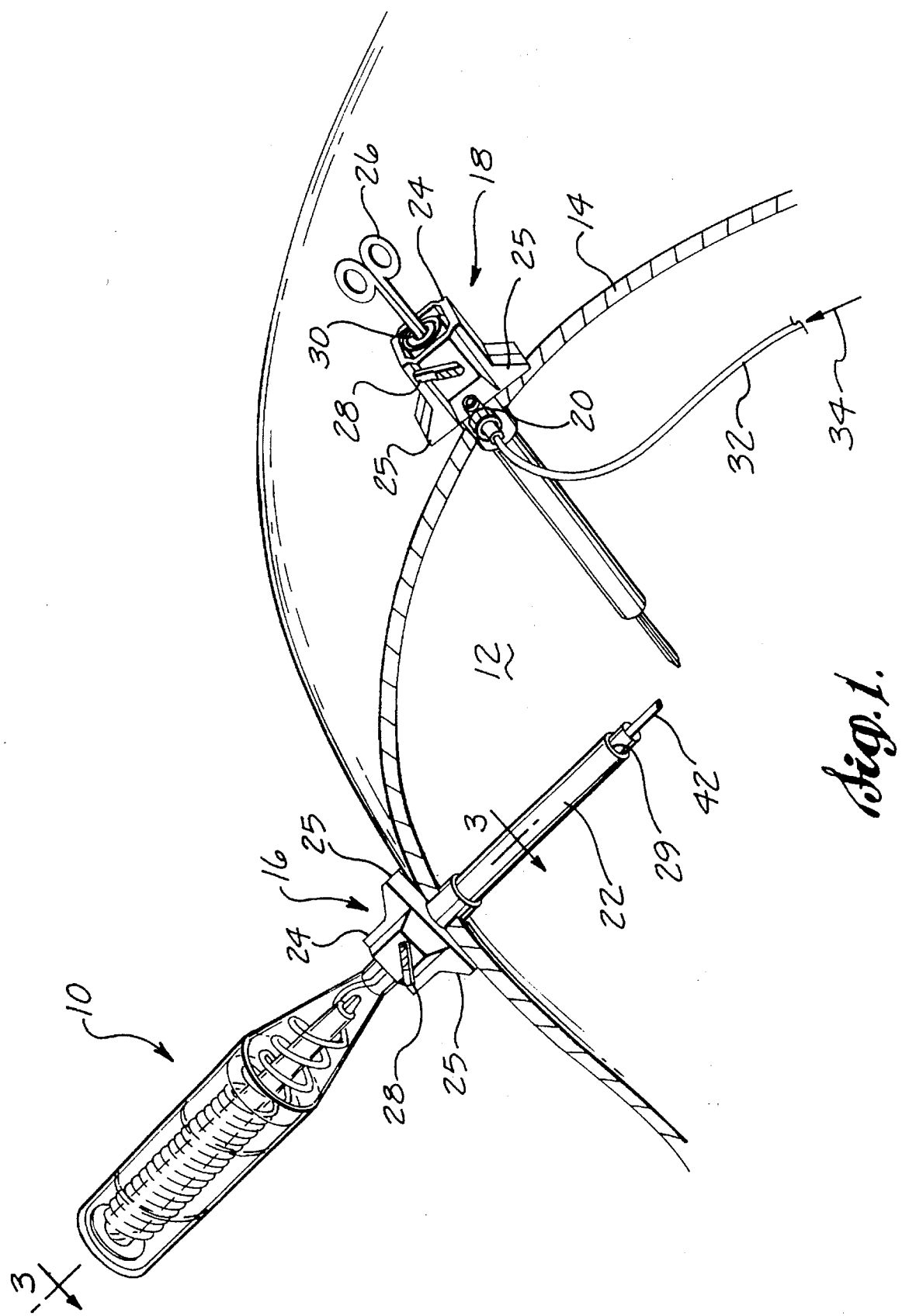
FIG. 1 illustrates a delivery device constructed in accordance with the present invention, being used to introduce a drain tube into the body of a patient.

A first preferred embodiment of the current invention is shown in FIG. 1 as an intra-abdominal cavity delivery device 10, along with a representation of a patient's intra-abdominal cavity 12. This is the area contained within a patient's abdomen, that is, the area behind the abdominal wall 14 where internal organs are located. Also shown in FIG. 1 are two laparoscopic operating ports 16 and 18. Laparoscopic operating ports 16 and 18 may be identical except that laparoscopic operating port 18 includes a valve 20, for the introduction of pressurization gas into the intra-abdominal cavity 12 of the patient. Also, the port 18 may be of a size smaller than the port 16.

Laparoscopic operating ports 16, 18 both include a cylindrically shaped, hollow tube 22 extending forwardly from an enlarged body portion 24. The body portion 24 is generally rectangular in shape. At the forward end of the body portion 24, adjacent the hollow tube 22, are two shoulders 25, on opposite sides of the body portion 24. Each shoulder is generally in the shape of a right triangle to present an abutment for the user's fingers when grasping the port. The hollow tube 22 mates with the body portion 24 so that the longitudinal axes of each part are coincident.

Each body portion 24 of the laparoscopic operating ports 16, 18 have an internal passageway 29 extending through it coincident with the longitudinal axis of the body portion. A laparoscopic surgical instrument 26 and the delivery device 10 are shown inserted into the internal passageway 29 of laparoscopic operating ports 18 and 16, respectively. The hollow tube 22 mates with the body portion 24 of the laparoscopic operating port 16, 18, such that internal passageway 29 extends from hollow tube 22 through body portion 24 of the laparoscopic operating port.

Both laparoscopic operating ports 16, 18 have an internal gate valve, not shown, for closing off the internal passageway 29 within the body portions 24. Pivot handles 28 are provided for manually operating the valves. When the valve is closed, its handle 28 is positioned generally perpendicularly to the longitudinal axis of hollow tube 22 and body portion 24. Ideally, the valve is spring biased in closed position. When the handle 28 is rotated clockwise approximately 30°, the valve is opened. In FIG. 1, laparoscopic operating ports 16, 18 have the delivery device 10, and the surgical instrument 26 inserted through them, respectively. Therefore, the valve handles 28 are shown in the open position.

As previously mentioned, laparoscopic operating port 18 contains a second valve 20 to open and close a small passageway, not shown, that perpendicularly intersects the first internal passageway 29 previously described. The smaller passageway is used to introduce inflation gas into the intra-abdominal cavity 12.

A lip seal 30 is located just inside rearward the entrance to the internal passageway 29, in the body portion 24 of laparoscopic operating ports 16, 18. Seal 30 is generally annularly shaped and surrounds the internal passageway 29. Seal 30 is designed to extend around instruments that are inserted into laparoscopic operating ports 16, 18 through valve 28 as long as the exterior size of the instrument closely corresponds with the interior size of the port to prevent fluid leakage through passageway 29 of the laparoscopic operating ports 16, 18 and into the environment.

The laparoscopic operating ports 16 and 18 are shown in FIG. 1 as partially inserted into the intra-abdominal cavity 12 of a patient. Note that each laparoscopic operating port 16, 18 is only inserted into the intra-abdominal cavity 12 up to near the body portion 24. The remaining portions of the laparoscopic operating ports 16, 18 are disposed outside the body of the patient.

Valve 20 on laparoscopic operating port 18 is shown attached to a delivery tube 32. The other end of the tube 32, in turn, connects to a source of pressurization gas 34. When valve 20 on laparoscopic operating port 18 is open, pressurization gas flows from source 34, through tube 32, through valve 20, and through the laparoscopic operating port 18 into the intra-abdominal cavity 12 of the patient. The intra-abdominal cavity 12 is normally pressurized in this way with carbon dioxide during a laparoscopic surgery to approximately 15 mm Hg. This properly inflates the intra-abdominal cavity 12, permitting medical procedures to be more easily accomplished within the intra-abdominal cavity.

In FIG. 1, as described above, an instrument 26 is shown inserted through laparoscopic operating port 18 and into the intra-abdominal cavity 12 of the patient. The seal 30, within the internal passageway of the port, presses against the circumference of the instrument 26 as it is inserted into the port and substantially prevents pressurization gas from escaping through the port while instrument 26 is being used.

The other laparoscopic operating port 16 is shown inserted substantially in the same manner as laparoscopic operating port 18. However, as mentioned previously, laparoscopic operating port 16 does not have valve 20 to connect to a source 34 of pressurization gas. This is because it is only necessary to pressurize the intra-abdominal cavity 12 of the patient through one laparoscopic operating port 18. Thus, there is no need to include a valve 20 to pressurize the intra-abdominal cavity 12 on laparoscopic operating port 16.

The foregoing description has concerned mainly the laparoscopic operating ports 16, 18, both of which are known in the art. The following discussion focuses on a preferred embodiment of the present invention.

In FIG. 1, a delivery device 10 constructed in accordance with the present invention is shown inserted through laparoscopic operating port 16. The purpose of the device is to deliver solid objects into intra-abdominal cavity 12 through laparoscopic operating port 16, while substantially preventing pressurization gas from escaping through the laparoscopic operating port.

Figure 2:
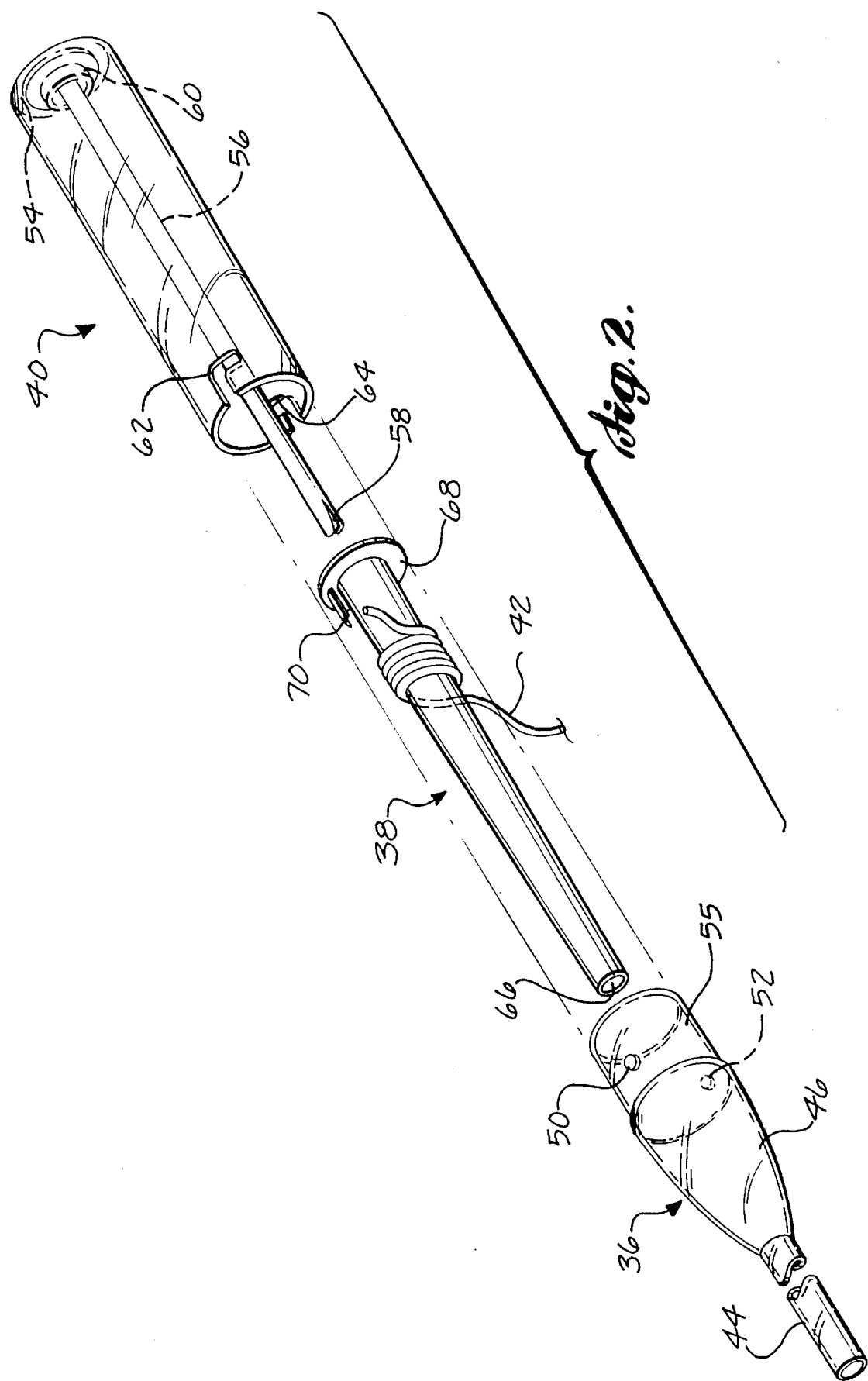
FIG. 2 illustrates the delivery device of FIG. 1 in an exploded view, along with the object to be introduced.
Figure 3:
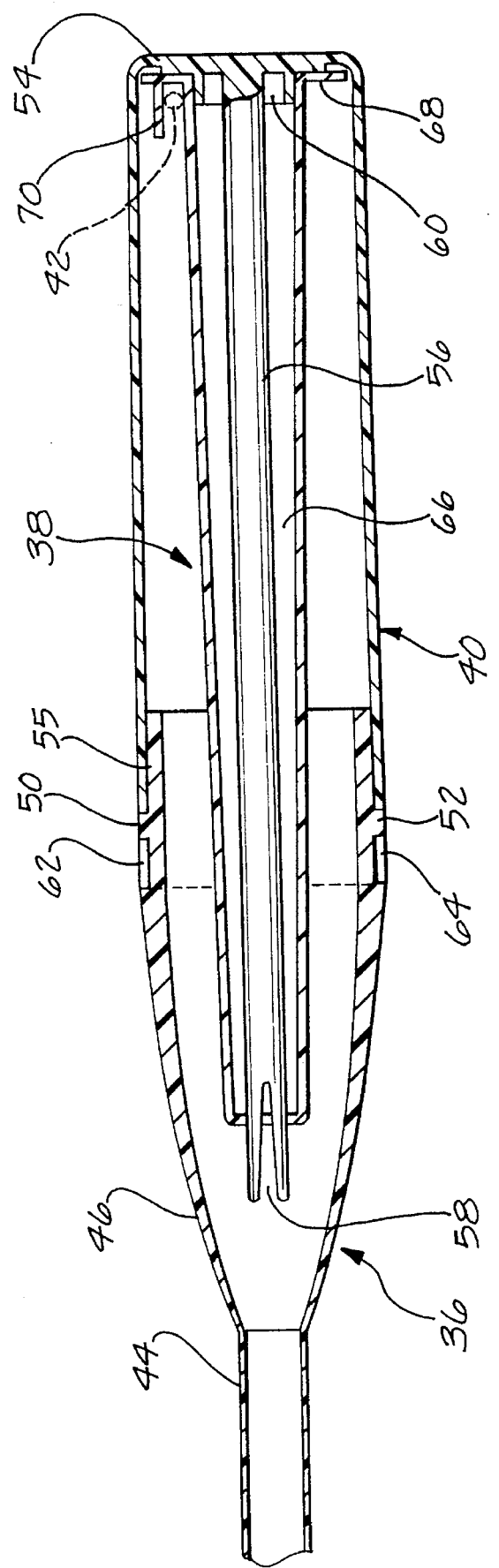
FIG. 3 is a cross-sectional view of a portion of FIG. 1, with the drain tube removed, taken substantially along lines 3—3 of FIG. 1; and, FIGS. 4 and 5 illustrate other embodiments of delivery devices constructed in accordance with the present invention.

FIGS. 2 and 3 show the three major components of the delivery device 10: a generally funnel-shaped end cap 36; an elongate, tapered spool 38; and, a cylindrical magazine 40. In addition, an object (drain tube 42) which is to be inserted into the intra-abdominal cavity 12 of a patient is shown.

The end cap 36 is generally in the shape of a funnel. The end cap includes an elongate, forward, tubular nose section 44, and a rearward body portion 46 that is generally cylindrical, but tapered or funnel-shaped at its intersection with the nose section 44. Tubular nose section 44 ideally is somewhat longer than the entire length of laparoscopic operating port 16. Thus, when nose section 44 is fully inserted into laparoscopic operating port 16, the tubular nose section extends forwardly out the end of hollow tube section 22 on laparoscopic operating port 16. A pair of diametrically opposite pins 50 and 52 project outwardly from the body portion 46 near the rearward end thereof. The purpose of these pins is described infra.

A second major component of delivery device 10 is a magazine 40, which ideally is generally cylindrical in shape. The rearward end of the magazine 40 (opposite nose section 44) is closed off by a rear wall 54. The inside diameter of the magazine 40 is substantially equal to that of the exterior diameter of a shoulder 55 formed at the rear of body portion 46. Ideally, these two components are designed to snugly engage each other.

Located coincidentally with the longitudinal axis of magazine 40 is an elongate rod 56. Rod 56 is mounted internally in magazine 40 so that it is cantilevered forwardly from the center of the rear wall 54 of the magazine. Rod 56 is ideally somewhat longer than the length of magazine 40 to extend a distance beyond the forward open end of the magazine. A cross split 58 is formed in the forward, free end of rod 56. The split 58 extends for a short distance rearwardly along rod 56, and each half of the rod at split 58 flares outwardly beyond the outer diameter of the rest of the rod. Rod 56 ideally is composed of material with some resilience or elasticity. Thus, if the split halves are pinched together and then released, the split halves will substantially return to their original positions.

Magazine 40 is designed to snugly mate with the end cap 36. The rearward shoulder 55 of the end cap 36 slides into the forward open end of magazine 40. When magazine 40 is closed off by end cap 36, a substantially airtight seal is formed between magazine 40 and the end cap 36.

L-shaped cutouts 62 and 64 are formed in diametrically opposite sides of the forward portion of the magazine 40. When the end cap 36 is slid into magazine 40, pins 50 and 52 of the end cap slide within the entrance portions of the L-shaped cutouts 62 and 64, respectively, that extend longitudinally along the magazine. When the pins 50 and 52 reach the intersection of the two legs of the L-shaped cutouts, magazine 40 and end cap 36 are rotated about their longitudinal axes in opposite directions such that pins 50 and 52 are shifted to the "bottoms" of the cutouts 62 and 64, whenever an end cap 36 is locked into engagement with magazine 40 in a substantially airtight manner.

Another major component of delivery device 10 is an elongate hollow spool 38. Spool 38 is ideally in the shape of a forwardly tapered cylinder having a longitudinal through bore 66 that engages over rod 56. When spool 38 is engaged on rod 56, the larger diameter rearward end of the spool is centered about rod 56 by a circular flange 60 extending forwardly from the end wall 54 of the magazine 40. Also, ideally, the rear end of the spool 38 loosely engages over the flange 60 to enable the spool to rotate about the flange 60 as discussed in more detail below. Ideally, the spool 38 tapers down in the forward direction so that at its forward end, the spool engages against the forward split end 58 of the rod 56.

Spool 38 is slid over rod 56 by squeezing the two split ends 58 together. Ideally, spool 38 is slightly shorter in length than rod 56. Thus, when spool 38 is mounted on rod 56, the split halves 58 extend outward beyond the forward end of spool 38, and the split halves substantially return to their original position. In this way, spool 38 is retained on the rod 56 because the diameter of bore 66 at the forward end of the spool is smaller than the envelope of the split end of the rod 56 is in its normal position. Sufficient clearance exists between the rod 56 and the spool bore 66 to enable the spool 38 to rotate freely on the rod while retaining the spool on the rod.

An annular flange 68 extends around the larger, rear end of the spool 38. When the spool 38 is engaged over rod 56, the flange 68 is in face-to-face contact with the rear wall 54 of magazine 40. A tab 70 extends forwardly a short distance from the flange 68, the function of which is described infra.

The delivery device 10 is used to insert flexible, solid objects into the intra-abdominal cavity 12 of a patient. One such type of object is an elongate drain tube 42, as shown in FIGS. 1 and 2. The drain tube 42 is loaded onto spool 38 by winding the drain tube around the spool. This may be accomplished by placing the distal end (the end to be positioned at the suction/drain site) of the drain tube 42 underneath the tab 70 on flange 68, to hold this end of the drain tube in place while the rest of the drain tube is wound around the spool. A short section of the proximal end of the drain tube (the end to be connected to the suction source), though long enough to extend through end cap 36 and out nose section 44, is left unwound. Then, spool 38 is engaged over rod 56 in magazine 40, and as end cap 36 is coupled to the magazine, the short section of drain tube 42 is threaded through the nose section 44. Thus, when end cap 36 is locked in place on magazine 40, a short portion of drain tube 42 extends out of the end of nose section 44. In this configuration, delivery device 10 is ready to deliver the drain tube 42 through laparoscopic operating port 16, and into the intra-abdominal cavity 12 of a patient. This delivery is accomplished in the following manner.

The nose section 44 of end cap 36 is inserted into laparoscopic operating port 16, which has previously been inserted into the intra-abdominal cavity 12 of a patient, as shown in FIG. 1. Insertion of the nose section 44 into the body portion 24 of the device 10 causes the gate valve therein to open. The outer diameter of nose section 44 is ideally only slightly smaller than the diameter of the internal passageway 29 in laparoscopic operating port 16, and thus the nose section seals against seal 30, located just inside the entrance to the internal passageway. Thus, when nose section 44 is inserted into laparoscopic operating port 16, a substantially airtight connection is made between the nose section and the operating port which prevents pressurization gas in the intra-abdominal cavity 12 from escaping through the laparoscopic operating port.

Referring to FIG. 1, when the delivery device 10 is in use, nose section 44 extends slightly beyond the forward end of the hollow tube 22 of laparoscopic operating port 16. Also, ideally, the drainage tube 42 extends slightly beyond nose section 44 of device 10 to project slightly into the intra-abdominal cavity 12 of the patient. Instrument 26, which has been inserted through laparoscopic operating port 18, may be used to grasp the projecting end of drain tube 42 and pull the drain tube into the intra-abdominal cavity thereby unwinding the drainage tube from spool 38. This procedure can be accomplished while substantially preventing the escape of pressurization gas from the intra-abdominal cavity 12 of the patient through laparoscopic operating port 16.

If laparoscopic operating ports 16 and 18 are not positioned so that the proximal end of the tube 42 can be easily grasped by instrument 26, the instrument 26 may be manually manipulated to more closely align the ports so that the end of tube 42 can be grasped by the instrument 26. After the drain tube has been unwound from the spool, the distal end of the drain tube may be positioned at the desired drainage site, e.g., at or adjacent the surgical site, by an appropriate instrument inserted into the port 16 after the delivery device 10 has been removed therefrom. The port 18 and the instrument 26, with the proximal end of the drain tube attached thereto, is then pulled out through the site of the port 18. If need be a surgical assistant can place his/her finger over the site from which the port 18 was removed to maintain the inflation of the intra-abdominal cavity.

FIG. 1 only shows two laparoscopic operating ports 16, 18 inserted into the intra-abdominal cavity 12 of a patient. However, other laparoscopic operating ports are also employed so that other instruments, such as a camera, may be used in the intra-abdominal cavity 12. Also, as a variation to the above procedures, the instrument 26 extending through port 18 can be used to grasp and retain the proximal end of the drain tube 42 when initially introduced into the intra-abdominal cavity. The rest of the tube 42 can thereafter be pulled through port 16 by a further instrument, not shown, similar to instrument 26 extending through a third port, not shown. This further instrument also can be used to position the distal end of tube 42 at the desired location. Thereafter, the instrument 26 with the proximal end of the tube 42 retained thereby and the corresponding port 18 may be withdrawn together to remove the excess length of the tube from the intra-abdominal cavity.

While a preferred embodiment has described a procedure for inserting a drainage/suction tube into the intra-abdominal cavity 12 of a patient, it is envisioned that substantially the same procedure may be used to deliver several other different kinds of objects to the surgical site. For example, this procedure can be used to insert a plastic specimen bag, fabric material for surgical repairs of a hernia, etc.

Figure 4:
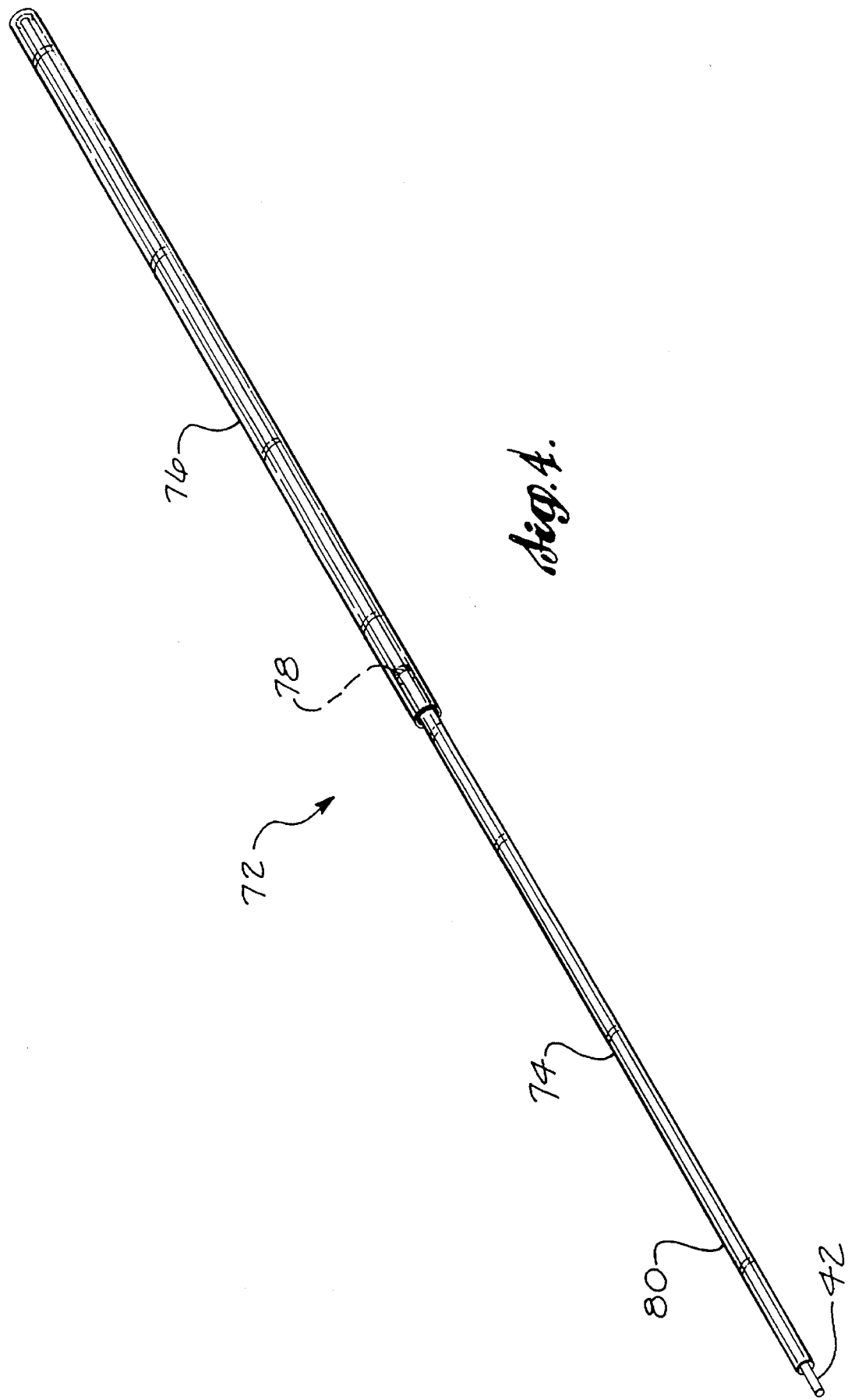

A second preferred embodiment in accordance with the present invention is shown in FIG. 4 as delivery device 72. Device 72 includes, inter alia, two elongate tubular sections 74 and 76 that are telescopically engaged. The smaller forward tubular section has an exterior diameter slightly smaller than the inside diameter of the tube section 22 of the access port 16 shown in FIG. 1.

The inside diameter of the rearward tubular section 76 is slightly larger than the outside diameter of the forward tube section 74. Thus, tube section 74 smoothly and snugly slides within tube section 76. A lip seal 78 extends around the outer circumference of the tube section 74 near the rearward end thereof to make continuous contact with the internal diameter of tube section 76 to form a substantially airtight seal between the two tube sections. The rear end of tubular section 76 is closed, while tube section 74 is open on both ends.

In operation, the delivery device 72 is used as follows. First, tube section 76 is disengaged from tube section 74. Then the object (drain tube 42) which is to be inserted into the intra-abdominal cavity 12 of the patient, is fed into tube section 76 until the distal end of the drain tube reaches the closed end of the tube section 76. The forward tube section 74 is then slid over the opposite, proximal end of tube 42 and slid along the drain tube until tube section 74 engages into tube section 76, thereby forming the substantially airtight seal therebetween. The tube section 74 is slid further onto tube 76 until a short portion of the proximal end of the drain tube 42 extends beyond the forward end 80 of tube section 74.

The device 72 is then inserted into the laparoscopic operating port 16, which has previously been inserted into the intra-abdominal cavity 12 of a patient, until tube section 74 extends just beyond the forward end of the tubular section 22 of the port within the intra-abdominal cavity 12 of a patient. Then tube section 76 is telescopically slid forwardly over the tube section 74, thereby expelling the drain tube 42 into the intra-abdominal cavity 12 of the patient. As with previously described embodiments of the present invention, an instrument 26 inserted through access port 18 is used to grasp the drain tube 42 and pull the tube into the intra-abdominal cavity. The distal end of the drain tube is then positioned at the surgical site as described above.

This method describes one way of using delivery device 72 to insert a particular object into the intra-abdominal cavity 12 of a patient while substantially preventing the escape of gas through laparoscopic operating port 16. Delivery device 72 can be used to insert other types of objects into the intra-abdominal cavity 12 of a patient.

Figure 5:
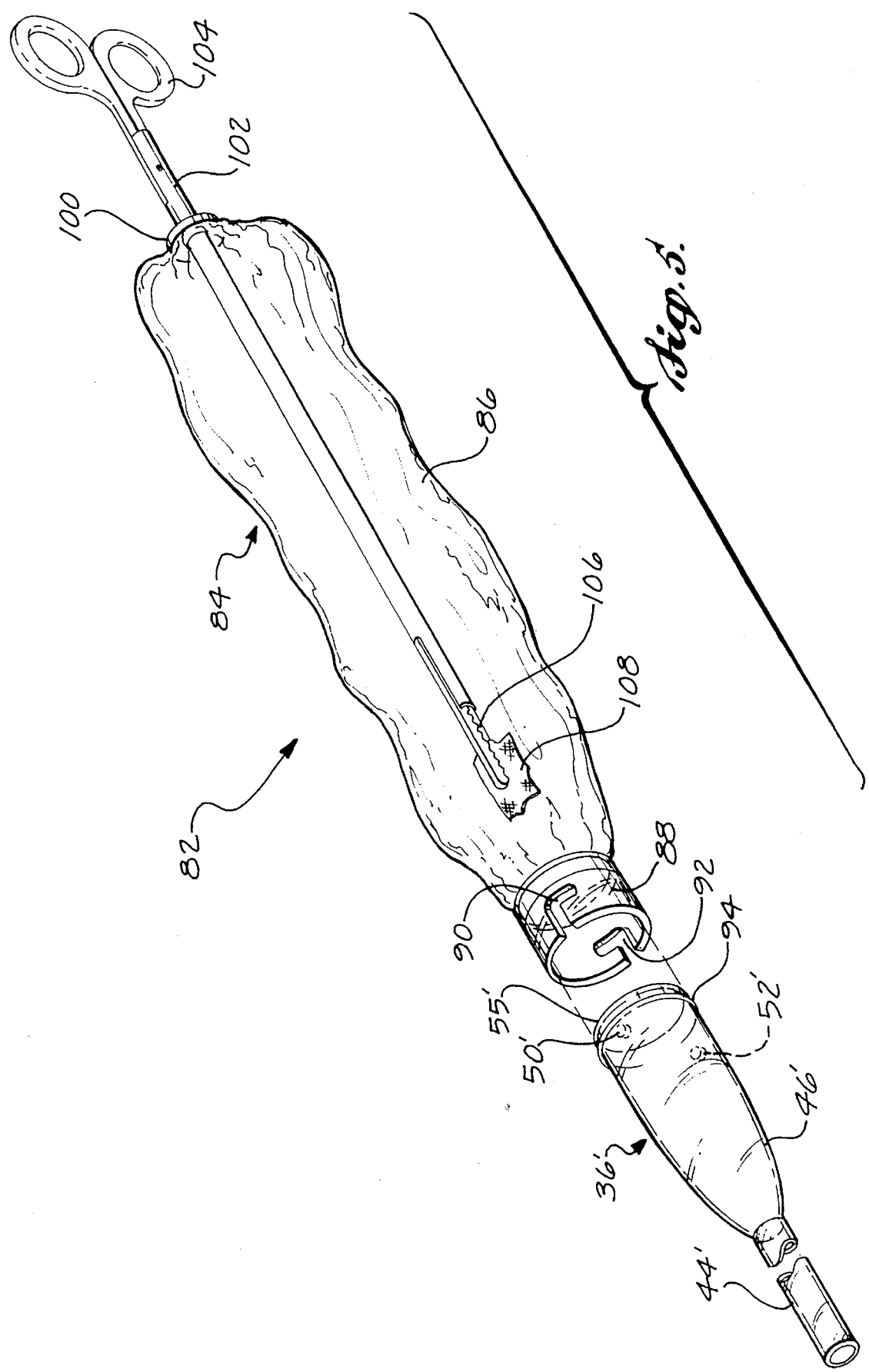

A further embodiment of the present invention includes a delivery device 82 as illustrated in FIG. 5. Delivery device 82 has an end cap 36' that may be identical to end cap 36 previously described in conjunction with FIGS. 1–3, and thus, corresponding components are identified with the same port number but with the addition of a prime ("'") designation. However, the delivery device shown in FIG. 5 utilizes a differently constructed magazine 84 than the magazine 40 shown in FIGS. 1–3.

In the embodiment of the present invention shown in FIG. 5, magazine 84 includes bag section 86 composed of a flexible, collapsible, and ideally transparent or translucent material. The leading, open end of the bag 86 is secured to a collar fitting 88. The inside diameter of fitting 88 is sized to snugly receive the shoulder portion 55' of the end cap 36'. Fitting 88 mates with end cap 36' in the same way that magazine 40 mates with the end cap 36. That is, pins 50' and 52', extending radially oppositely from end cap 36', engage into L-shaped cutouts 90 and 92 on fitting 88 until the pins reach the intersection of the two legs of the L-shaped cutouts. Thereupon, the end cap 36' and fitting 88 are rotated in opposite directions, thereby engaging the pins 50' and 52' in the transverse section of the L-shaped cutouts 90 and 92 until the pins "bottom out" at the closed end of the cutouts, thereby locking the end cap 36' into fitting 88. A substantially airtight seal is formed between end cap 36' and fitting 88 due to a gasket 94 mounted on the end cap which makes continuous contact with the circumference of the end cap 36' and the internal circumference of fitting 88.

Located at the rear end of the magazine bag 86 is a second fitting 100 having a central aperture to receive a close fitting rod like instrument 102. Instrument 102 is inserted longitudinally through fitting 100 so that part of the instrument is inside of bag 86 and part of the instrument remains outside of bag 86. Instrument 102 is sealed in a substantially airtight manner to fitting 100. The rearward end of instrument 102 that remains outside of bag 86 may include handles 104.

The opposite leading end of the instrument 102—that is, the end of instrument 102 shown in FIG. 5 to be within bag 86—includes a jaw 106. Jaw 106 is used to hold objects which are to be inserted into the intra-abdominal cavity 12 of a patient. The jaw 106 is normally closed thereby to tightly grasp the object which is to be inserted into the patient.

The delivery device 82 is used in the following manner. Before the end cap 36' is engaged with the fitting 88, the object which is to be inserted into the intra-abdominal cavity 12 of the patient is placed in the jaw 106 of the instrument 102. If the object has a relatively large, flexible structure, a portion of the object may be inserted into the jaw and the rest of the object may be wound around the instrument 102. In FIG. 5, jaw 106 is shown holding a piece of fabric 108 to be used in repairing a hernia tear.

The end cap 36' is engaged with the magazine 84. Next, the nose section 44' of the end cap 36' is inserted into laparoscopic operating port 16 that has previously been inserted into the intra-abdominal cavity 12 of the patient, as shown in FIG. 1. The end cap 36' is inserted into laparoscopic operating port 16 until nose section 44' extends slightly beyond the leading end of tube 22. Once the delivery device 82 is in place, that is, inserted into laparoscopic operating port 16, instrument 102 may be pushed through the end cap 36', and the nose section 44' thereof into the intra-abdominal cavity 12 of the patient. As the insertion of the instrument 102 occurs, the fabric 108 can collapse about the instrument. It will be appreciated that as with the embodiments of the present invention described previously, the embodiment shown in FIG. 5 also allows various objects to be safely and conveniently inserted within the intra-abdominal cavity of the patent without any significant escape of gas used to inflate the intra-abdominal cavity.

It is readily apparent to one skilled in the art, that delivery device 82 can be used to insert many types of objects into the intra-abdominal cavity 12 of a patient. Not only can objects of a flexible structure be inserted, such as fabric or tubes, etc., but also rigid objects.

While several preferred embodiments of the present invention have been illustrated and described, it will be appreciated that various changes can be made without departing from the spirit and scope of the present invention. For example, in the preferred embodiment shown in FIG. 5, instead of using a flexible bag 86 as part of magazine 84, the bag could be eliminated and fitting 88 could be extended to form a cylindrical magazine. Instrument 102 could still be used to introduce objects through the end cap 36' and into the intra-abdominal cavity 12. Thus, instrument 102 could be used in substantially the same manner as in the embodiment shown in FIG. 5.

Also, in the embodiment of the present invention shown in FIGS. 1–3, the spool 38 and thus also the rod 56, could be eliminated so that the interior of the magazine 40 is essentially empty. The tube 42, or other object to be delivered, could be simply coiled about itself or otherwise stored within the magazine until delivery occurs.

An important aspect of the various embodiments of the present invention described above is that they can be used to insert solid objects through laparoscopic operating ports 16, 18 while substantially preventing the escape of inflation gas from the intra-abdominal cavity 12 through the laparoscopic operating ports. To this end, ideally the portions of the delivery device 10 that are inserted into the laparoscopic operating port (the nose section 44 of end cap 36) are only slightly smaller in diameter than the hollow tube 22. This helps to ensure that the inserted portion of the delivery device substantially contacts the seal 30 just inside the internal passageway in laparoscopic operating ports 16, 18. Thus, a substantially airtight seal is formed between the inserted delivery device and the laparoscopic operation port.

Also, the delivery device is only open on one end to permit expulsion of the object being delivered, while the rest of the device is substantially airtight. Thus, gas used to inflate the intra-abdominal cavity does not escape through the delivery device. A further significant aspect of the present invention is that the delivery device is able to securely hold the object to be inserted into the intra-abdominal cavity 12 of the patient prior to the delivery actually occurring.

The embodiments of the invention in which an exclusive property or privilege is claimed are defined as follows:

1. An apparatus for introducing a solid object into the intra-abdominal cavity of a patient during a medical procedure through an access port previously inserted into the intra-abdominal cavity, comprising:

(a) magazine means having opposite first and second ends, the first end being substantially sealed, and the second end being open, for substantially containing the object prior to introduction of the object into the intra-abdominal cavity, wherein the magazine means contains a spool mounted within the magazine means for wrapping the object around the spool prior to introduction of the object into the intra-abdominal cavity of the patient, and thereafter for unwrapping the object from the spool during introduction of the object into the intra-abdominal cavity of the patient, wherein the spool is engageable over a spindle forming an axis for the spool and wherein the spindle is mounted within the magazine means; and (b) connection means connected to the magazine means for connecting the magazine means to the access port to permit withdrawal of the object from the magazine means and delivery into the intra-abdominal cavity, the connection means including a first, forward end insertable into the access port.

2. The apparatus as in claim 1, wherein clearance is provided between the spool and the spindle to permit the spool to rotate on the spindle.

3. The apparatus of claim 2, further comprising means for retaining the spool on the spindle and simultaneously permitting the spool to rotate on the spindle.

4. The apparatus as in claim 3, wherein:

(a) the spindle includes a forward end and a generally cylindrical body portion having an outer diameter; and (b) the means for retaining includes a cross split formed in the forward end of the spindle, the cross split forming two halves that nominally flare outwardly beyond the outer diameter of the cylindrical body portion to retain the spool on the body portion, while permitting the removal of the spool from the body portion when the two halves are pressed together.

5. An apparatus for introducing a flexible tube into the intra-abdominal cavity of a patient through an access port previously inserted into the intra-abdominal cavity, the port having an internal passageway, and the tube having a distal end and a proximal end, the apparatus comprising:

(a) a magazine having a substantially sealed proximal end, and an open distal end of a first cross-sectional area;

(b) a tube, wherein the proximal end of the tube is housed within the magazine prior to introduction of the tube into the intra-abdominal cavity of the patient; and (c) a cap for capping the magazine, the cap comprising:
  (i) an elongated, hollow nose section having a distal end portion of a second cross-sectional area substantially smaller than the first cross-sectional area for slidable insertion of the nose section into and through the port, and also having a proximal end portion; and
  (ii) an enlarged, hollow base section attached to and in communication with the proximal end portion of the nose section, the base section having an enlarged cross-sectional area matching the first cross-sectional area;

(d) connecting means for disengageably locking the base section of the cap into engagement with the distal end of the magazine; and (e) whereby a continuous passageway is defined from the distal end of the magazine through the base section of the cap and through the nose section of the cap.

6. The apparatus according to claim 5, further comprising:

(a) a spool disposed within the magazine for paying out the tube which is adapted to be been previously around the spool prior to introduction of the tube into the intra-abdominal cavity of the patient; and, (b) means for mounting the spool within the magazine for rotation of the spool as the tube is payed out.

* * * * *

UNITED STATES PATENT AND TRADEMARK OFFICE
CERTIFICATE OF CORRECTION

PATENT NO. : 5,545,169
DATED : August 13, 1996
INVENTOR(S) : R.J. Yarger

It is certified that error appears in the above-indentified patent and that said Letters Patent is hereby corrected as shown below:

COLUMN   LINE

12            17          Delete "been previously" and insert --wrapped--
(Claim 6,  line 3)

12            21          "is payed" should read --is being payed--
(Claim 6,  line 7)

Signed and Sealed this

Twenty-second Day of April, 1997

BRUCE LEHMAN

*Attest:*

*Attesting Officer*      Commissioner of Patents and Trademarks